|  | United States Patent [19] | [11] | Patent Number: | 5,076,093 |
|---|---|---|---|---|
|  | Jones, Jr. et al. | [45] | Date of Patent: | Dec. 31, 1991 |

[54] FLOW VOLUME CALIBRATOR

[76] Inventors: William C. Jones, Jr.; William C. Jones, Sr., both of 200 Windsor Dr., Oak Brook, Ill. 60521

[21] Appl. No.: 579,187

[22] Filed: Aug. 29, 1990

Related U.S. Application Data

[63] Continuation of Ser. No. 234,317, Aug. 19, 1988, abandoned.

[51] Int. Cl.⁵ ............................................. G01F 25/00
[52] U.S. Cl. ......................................................... 73/3
[58] Field of Search .................... 73/3, 239, 242, 248, 73/249, 251, 252; 128/725–729; 250/231.13, 231.14, 231.16, 231.15, 231.17

[56] References Cited

U.S. PATENT DOCUMENTS

| 3,512,521 | 5/1970 | Jones . |  |
|---|---|---|---|
| 3,977,394 | 8/1976 | Jones et al. . |  |
| 4,203,316 | 5/1980 | Jones . |  |
| 4,224,281 | 9/1980 | Thieme et al. | 73/864.18 |
| 4,250,890 | 2/1981 | Jones et al. . |  |
| 4,324,127 | 4/1982 | Gazzara et al. . |  |
| 4,421,120 | 12/1983 | Edwards, Jr. et al. . |  |
| 4,475,666 | 10/1984 | Bilbrey et al. | 604/155 |
| 4,908,017 | 3/1990 | Howson et al. | 604/67 |

Primary Examiner—Robert Raevis
Attorney, Agent, or Firm—Tilton, Fallon, Lungmus & Chestnut

[57] ABSTRACT

An apparatus for calibrating a spirometer controls the temperature and moisture content of the gas which it receives and accurately measures the flow rates of gas it receives and discharges. This apparatus includes a housing with an opening through which it receives and discharges the gas. This housing contains a piston which engages the inner surface of the housing to form a gas receiving chamber within the housing. The piston lies in sliding engagement in the housing and a user may move it to increase or decrease the volume of the chamber and pull gas into the chamber through the opening or force gas out of the chamber. A heating element disposed proximate the chamber heats the gas which the chamber receives; and a gas moisturizing element disposed in the housing adds moisture to the gas moving into the chamber and out of the chamber through the housing opening. The apparatus also includes a displacement detecting assembly for measuring the displacement of the piston to measure the flow of gas out of the chamber and into it.

7 Claims, 2 Drawing Sheets

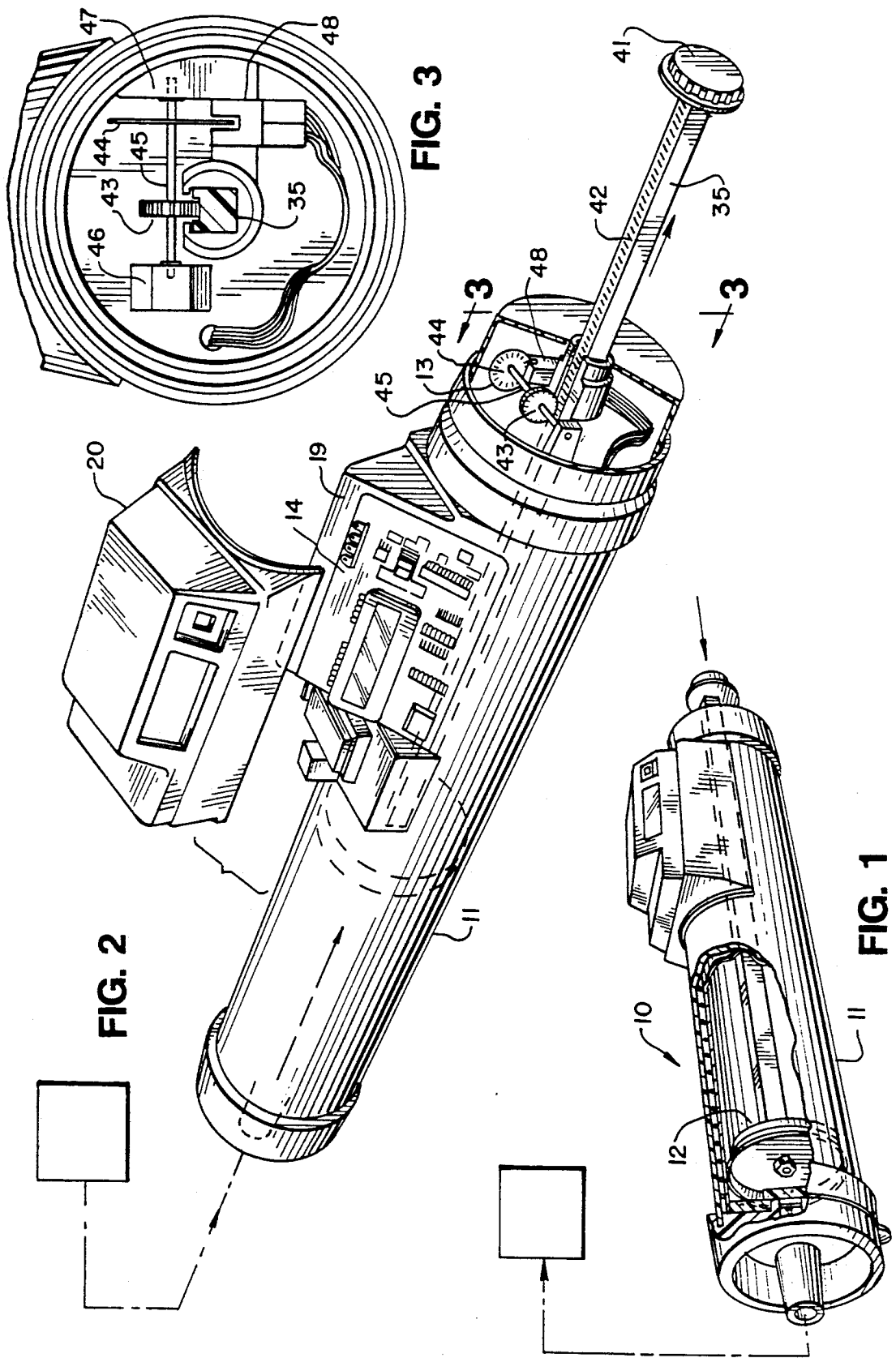

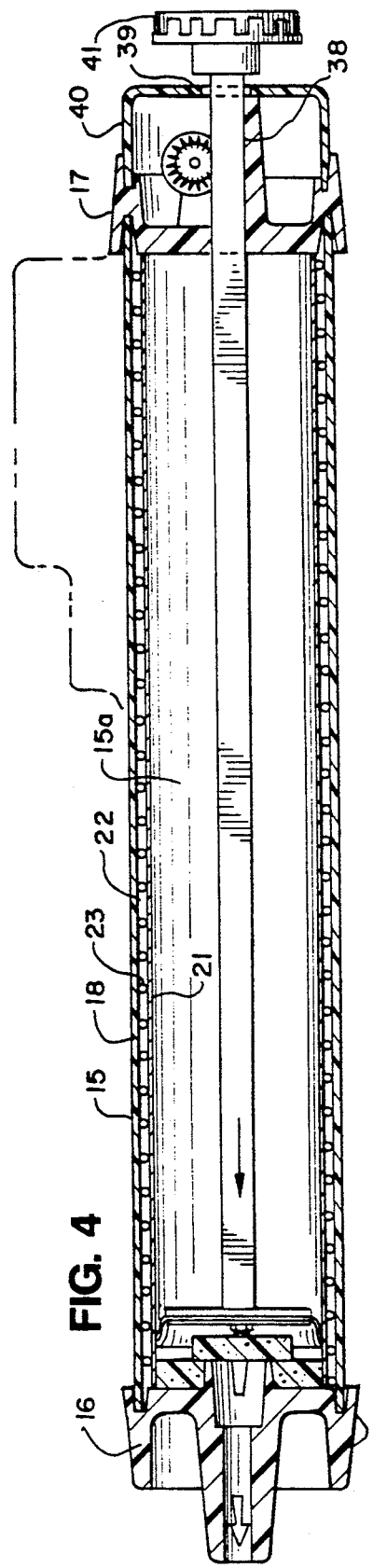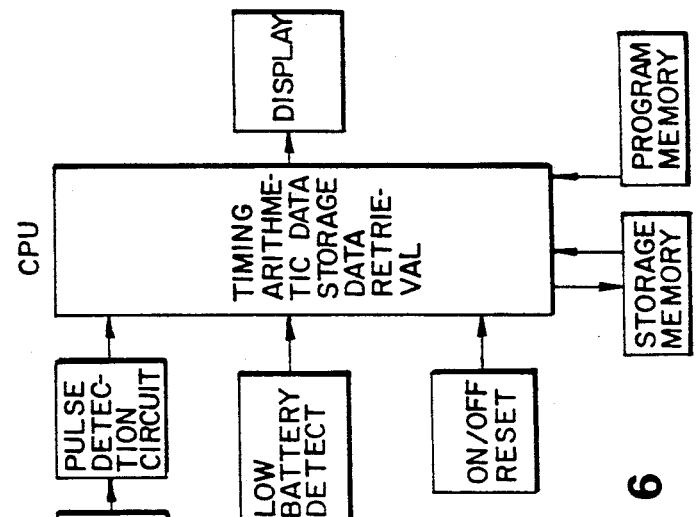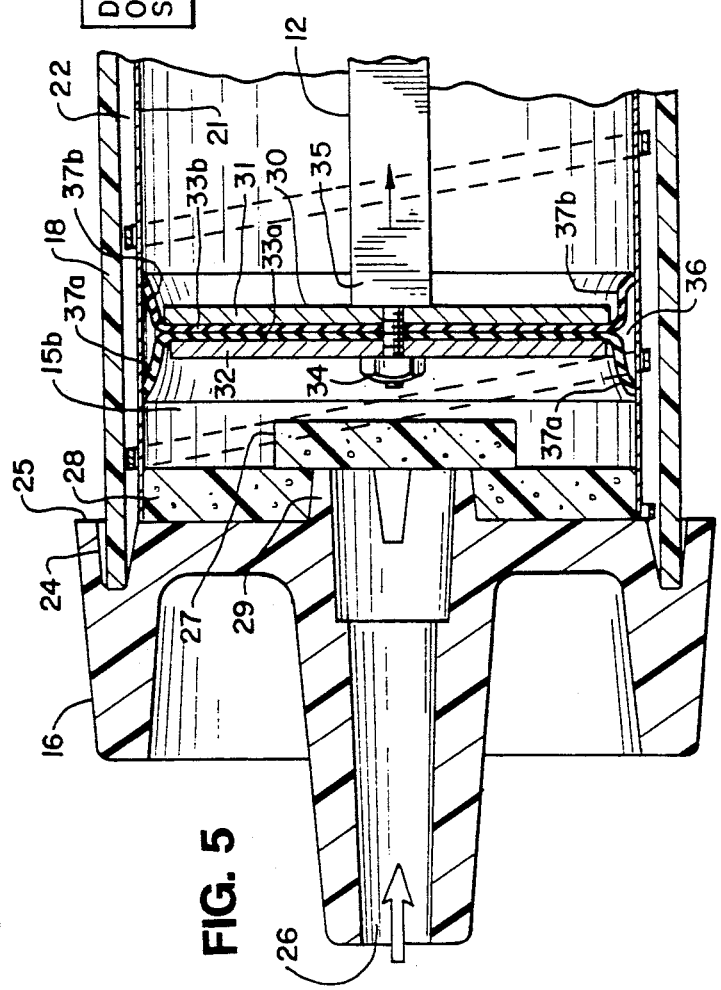

FLOW VOLUME CALIBRATOR

This application is a continuation, of application Ser. No. 234,317, filed Aug. 19, 1988, now abandoned.

BACKGROUND OF THE INVENTION

1. Field Of The Invention

The present invention relates generally to a flow volume calibrator for a spirometer and, more specifically, to a flow volume calibrator which provides accurate calibration of spirometers by controlling the temperature and moisture content of gas which it receives and accurately measuring the flow rates of gas it receives and discharges.

2. Description Of The Prior Art

In recent years, machinery for evaluating lung function, e.g., spirometers, has experienced commercial success and has found wide acceptance and application. Generally, this machinery measures the forceful exhalation or inhalation of a patient's breath, i.e., the volume of air inhaled or exhaled by a patient over a certain time period. It must consistently perform these measurements with a high degree of accuracy.

To insure the accuracy of spirometers and similar apparatus, those working in the art have proposed a number of calibration devices which produce an exhalation or inhalation action having predetermined characteristics which a user may compare to the output of the spirometer. Desirably, these devices should provide gas having the same temperature and moisture level as the breath of a patient. In addition, they should provide flow rates for a wide variety of volumes.

One known device is a large syringe that provides a predetermined volume of air for calibrating a spirometer. To measure the time which it takes to force the volume of air contained by the syringe into the spirometer, the user must coordinate the movement of the syringe's plunger with a timer. Since many acceptable standards require testing at time intervals of a second or less, a user cannot obtain accurate time and volume readings. In addition, this prior calibrator does not adjust the temperature and moisture content of the gas it receives.

The calibrator of the present invention fulfills the requirements outlined above and avoids the shortcomings of the prior calibrators. It is a simple construction which can adjust the temperature and moisture content of the gas it receives and which provides flow rates for a wide variety of volumes.

SUMMARY OF THE INVENTION

In accordance with one embodiment of the invention, a flow volume calibrator, which calibrates spirometers, controls the temperature and moisture content of the gas which it receives and accurately measures the flow rates of gas it receives and discharges. The calibrator includes a housing with an opening through which the apparatus receives and discharges the gas. This housing contains a piston which engages the inner surface of the housing to form a gas receiving chamber within the housing. The piston lies in sliding engagement in the housing and a user may move it to increase or decrease the volume of the gas receiving chamber and pull gas into the chamber through the opening or force gas out of the chamber.

The calibrator also includes a heating element disposed proximate the chamber for heating the gas which the chamber receives. A gas moisturizing element disposed in the housing adds moisture to the gas moving into the chamber and out of the chamber through the housing opening. Finally, a displacement detecting assembly for measuring the displacement of the piston to measure the flow of gas out of the chamber and into it.

The displacement detecting assembly includes a rotating member and a drive assembly for translating the linear displacement of the piston to the rotational movement of the disc. A sensor measures this movement over time and provides continuous, bi-directional data to a data processor which converts the data to flow readings. The data processor displays these readings.

BRIEF DESCRIPTION OF THE DRAWINGS

For a more complete understanding of this invention, one should now refer to the embodiment illustrated in greater detail in the accompanying drawings and described below by way of an example of the invention. In the drawings:

FIG. 1 is a perspective view of the flow volume calibrator with a portion of the housing cut away to expose the piston disposed inside.

FIG. 2 is a perspective view of the calibrator with the control panel cover removed and with a portion of an end cap cut away to expose the sensing assembly used to detect the displacement of the piston.

FIG. 3 is a sectional view taken along line 3—3 in FIG. 2.

FIG. 4 is a sectional view taken along the longitudinal axis of the calibrator.

FIG. 5 is a partial, enlarged sectional view of the end of the calibrator which includes a port through which gas enters the calibrator and, through which it discharges.

FIG. 6 is a block diagram of the circuitry used in the calibrator.

While the following disclosure describes the invention in connection with a preferred embodiment, one should understand that the invention is not limited to this embodiment. Furthermore, one should understand that the drawings are not to scale and that the embodiment is illustrated in part by graphic symbols, diagrammatic representations and fragmentary views. In certain instances, the disclosure may not include details which are not necessary for an understanding of the present invention such as conventional details of fabrication and assembly.

DETAILED DESCRIPTION OF THE DRAWINGS AND A PREFERRED EMBODIMENT

Turning now to the drawings, FIG. 1 shows the preferred embodiment of a flow volume calibrator generally at 10. The calibrator 10 generally comprises a housing 11, a piston 12 disposed in the housing, a sensing assembly 13 (See FIG. 2) for detecting the displacement of the piston 12 and controls 14 for receiving the data from the sensing assembly 13 and generating volume and flow data.

The housing 11 includes a cylinder 15 defining a central bore 15a closed at one end by a cap 16 and at the opposite end by a cap 17 (See FIG. 4). The cylinder 15 includes a wall with an outer shell 18 formed of a hard plastic or any other suitable material of high strength, heat insulation, and rigidity. A panel 19 integrally formed with this shell 18 supports the controls 14; and a cover 20 having a configuration similar to that of the panel and formed of the same or similar material fits over the control panel to cover it and protect the controls 14. The cover 20 has suitably sized openings which allow the user to observe the displays of the computerized controls 14.

The wall of the cylinder 15 also includes a precisely drawn aluminum tube 21 disposed in the outer shell 18 (See FIG. 5). This tube has a constant diameter throughout its length and it defines the bore 15a. The outer diameter of the tube 21 is smaller than the inside diameter of the shell 18. This difference in diameters provides a space 22 between the tube 21 and the shell 18. A heating coil 23 wound around the heat conducting tube 21 lies in this space 22 and transfers heat to the gas which the calibrator 10 receives (as described below).

The cap 16 is a structural member formed of hard plastic or an other material of high strength and rigidity. It lies at one end of the cylinder 15 adhered or otherwise secured to the end of the cylinder 15 (See FIG. 5). (Cap 17 is made out of the same material and is similarly secured to the cylinder 15.) An annular groove 24 formed at the inner face 25 of the cap 16 receives the end portions of the cylinder 15 to insure a secure connection between the cap 16 and the cylinder 15. The cap 16 defines a port 26 which provides fluid communication between the inside and the outside of the calibrator housing 11. Through this port, the calibrator receives air. It also discharges air through this port after the heating element 23 has heated the air and after a pair of pads, 27 and 28, have moisturized it.

The pad 27 is a open-celled polyurethane foam layer which covers the inner end of the port 26. It receives moisture through this port 26 and transfers it to the air which also flows through the port. Similarly, the pad 28 has a ring-like configuration and it lies between the tube 21 and an annular protuberance 29 of the cap 16. Adhesive or any other suitable attaching means secures the pads 27 and 28 to the cap 16.

The piston 12 draws air into the housing 11 and pushes the air back out of it. It defines a chamber 15b between it and the cap 16. This chamber receives air when a user pulls the piston 12 back, away from the cap 16 (as described below). When the user pushes the piston 12 toward the cap 16, the air discharges out of the chamber 15b through the port 26.

The piston 12 includes a disc 30 formed by a first rigid, round plate 31, a second rigid, round plate 32, and two opposed flexible, rubber seals 33a and 33b having a round, plate-like configuration and disposed between the plates 31 and 32. A screw 34 which extends through the central openings (not shown) in these four members secures them to a rod 35. The plates 31 and 32 are made of a rigid, high strength material, e.g., metal, hard plastic. They have a diameter smaller than the inside diameter of the tube 21. This difference in diameters provides an annular space 36 between the disc 30 and the tube 21 to allow the piston 12 to move back and forth along the bore 15a. The seals 33a and 33b, however, have a diameter greater than the inside diameter of the tube 21. The portions of the flexible seals 33a and 33b which extend beyond the plates 31 and 32 are flaps 37a and 37b which brush up against the inner surface of tube 21 to provide an air tight seal between the piston and the tube 21. These flaps 37a and 37b maintain this seal continuously as the piston moves inside the bore 15a. The opposed flap 37a provides a gas tight seal in the chamber 15b when the piston 12 moves forward to exhaust air through the opening 26. Conversely, opposed flap 37b provides a gas tight seal when the piston 12 pulls air into chamber 15b through port 26 and moisturizer 27.

The rod 35 extends back away from the cap 16, through a central opening 38 in the cap 17, through an opening 39 in a cover 40 which covers the outer end of the cap 17, and out of the calibrator 10 (See FIG. 4). The rod 35 is made out of hard plastic or any other suitable material having high strength and rigidity; and it has a generally rectangular cross section and a rack 42 formed in its top surface. At the end which lies outside of the calibrator, the rod supports a handle 41 fixedly secured to it. Using this handle, one may move the piston 12 back and forth in the bore 15a.

The rod 35 drives a gear wheel 43 which meshes with the rack 42 (See FIG. 3). In driving the gear wheel 43, it also drives a disc 44 which, like gear wheel 43, lies fixedly secured to a shaft 45. The ends of the shaft 45 lie journaled in bearings secured to protuberances 46 and 47 of the cap 17; and the shaft 45 rotates freely about its longitudinal axis.

The gear wheel 43, disc 44, and shaft 45 translate the linear displacement of the rod 35 into rotational displacement of the disc 44; and a high speed, dual optical sensor 48 detects this rotational displacement. The disc 44 includes slots formed at precise intervals around its circumference. As the disc 44 rotates, the slotted portion moves through the light field of the sensor 48. The sensor 48 permits phase shift readings to discriminate motion, provides backup in the event of failure of one of the two sensors of the dual optical sensor, and identifies the direction of the motion, i.e., inspiratory or expiratory. It generates pulses which the circuitry uses to provide volume and flow rate readings throughout the entire range of movement of the piston 12.

The circuitry shown in FIG. 6 receives the pulses provided by the sensor 48 and processes them to provide volume and flow readings on its display. The pulse detection circuit detects pulses provided by the dual optical sensor; and the CPU stores them. The CPU then calculates volumes and flow rates using the stored pulses. It then outputs the data to a display for viewing. The sensor 48 and circuitry provide continuous and bi-directional sensing.

While the applicant has shown one embodiment of the invention, one will understand, of course, that the invention is not limited to this embodiment since those skilled in the art to which the invention pertains may make modifications and other embodiments of the principals of the invention, particularly upon considering the foregoing teachings. The applicants, therefore, by the appended claims, intend to cover any modifications and other embodiments which incorporate those features which constitute the essential features of this invention.

What is claimed is:

1. An apparatus for calibrating pulmonary function testing equipment, said apparatus comprising: a housing defining an opening for receiving and discharging a gas; piston means disposed in said housing in sliding engagement with the inner surface of said housing for combining with said housing to form a chamber, said piston means being moveable in said housing to increase or decrease the volume of said chamber; said opening in said housing providing communication between the chamber and the outside of said housing; heating means disposed proximate said chamber for heating the gas which the chamber receives through said opening; gas moisturizing means disposed in said housing for adding moisture to gas moving into and out of said chamber through said opening; displacement detecting means for continuously detecting the displacement of said piston to measure the flow of gas entering into said housing through said opening and discharging from said housing through said opening; said apparatus calibrating pulmonary function testing equipment.

2. An apparatus for calibrating pulmonary function testing equipment, said apparatus comprising: a housing defining an opening for receiving and discharging a gas; piston means disposed in said housing in sliding engagement with the inner surface of said housing for combining with said housing to form a chamber, said piston means being moveable in said housing to increase or decrease the volume of said chamber; said opening in said housing providing communication between the chamber and the outside of said housing; gas moisturizing means disposed in said housing for adding moisture to gas moving into and out of said chamber through said opening; said apparatus calibrating pulmonary function testing equipment.

3. An apparatus for calibrating pulmonary function testing equipment, said apparatus comprising: a housing defining an opening for receiving and discharging a gas; piston means disposed in said housing in sliding engagement with the inner surface of said housing for combining with said housing to form a chamber, said piston means being moveable in said housing to increase or decrease the volume of said chamber; said opening in said housing providing communication between the chamber and the outside of said housing; heating means disposed proximate said chamber for heating the gas which the chamber receives through said opening; gas moisturizing means disposed in said housing for adding moisture to gas moving into and out of said chamber through said opening; said apparatus calibrating pulmonary function testing equipment.

4. An apparatus for calibrating pulmonary function testing equipment, said apparatus comprising: a housing defining an opening for receiving and discharging a gas; piston means disposed in said housing in sliding engagement with the inner surface of said housing for combining with said housing to form a chamber, said piston means being moveable in said housing to increase or decrease the volume of said chamber; said opening in said housing providing communication between the chamber and the outside of said housing; gas moisturizing means disposed in said housing for adding moisture to gas moving into and out of said chamber through said opening; displacement detecting means for measuring the displacement of said piston to measure the flow of gas entering into said housing through said opening and discharging from said housing through said opening; said apparatus calibrating pulmonary function testing equipment.

5. The apparatus of claim 1, 2, 3, or 4 in which said housing is a closed, elongate cylinder with a central bore.

6. The apparatus of claim 1, or 3 in which said heating means includes a heating coil secured to said housing.

7. The apparatus of claim 1, 2, 3, or 4 in which said gas moisturizing means includes an open-celled polyurethane layer secured to said housing for receiving moisture and transferring it to gas moving through said layer.

* * * * *